US005629001A

United States Patent [19]
Michael et al.

[11] Patent Number: 5,629,001
[45] Date of Patent: May 13, 1997

[54] ORAL ADMINISTRATION OF THERAPEUTIC PROTEINS FOR TREATMENT OF INFECTIOUS DISEASE

[75] Inventors: J. Gabriel Michael; Allen Litwin, both of Cincinnati, Ohio

[73] Assignee: University of Cincinnati, Cincinnati, Ohio

[21] Appl. No.: 380,031

[22] Filed: Jan. 30, 1995

Related U.S. Application Data

[62] Division of Ser. No. 329,685, Oct. 26, 1994, which is a continuation of Ser. No. 178,503, Jan. 7, 1994, abandoned, which is a continuation-in-part of Ser. No. 994,932, Dec. 22, 1992, abandoned, which is a continuation of Ser. No. 719,160, Jun. 21, 1991, abandoned.

[51] Int. Cl.$^6$ .......................... A61K 39/00; A61K 9/32; A61K 9/16; A61F 13/00
[52] U.S. Cl. .................. 424/234.1; 424/184.1; 424/482; 424/464; 424/422; 424/497
[58] Field of Search .................. 424/234.1, 482, 424/464, 422, 184.1, 497

[56] References Cited

U.S. PATENT DOCUMENTS

| | | | |
|---|---|---|---|
| 4,016,254 | 4/1977 | Seager et al. . | |
| 4,017,647 | 4/1977 | Ohno et al. .................. | 427/3 |
| 4,348,384 | 9/1982 | Horikoshi et al. . | |
| 4,469,677 | 9/1984 | Michael et al. . | |
| 4,507,276 | 3/1985 | Tencza et al. . | |
| 4,642,232 | 2/1987 | Yman et al. . | |
| 4,704,295 | 11/1987 | Porter et al. ................. | 427/3 |
| 4,798,844 | 1/1989 | Fujita et al. .................. | 514/399 |
| 4,820,627 | 4/1989 | McGeehan et al. . | |
| 4,874,613 | 10/1989 | Hsiao et al. . | |
| 4,900,557 | 2/1990 | Dell et al. . | |
| 4,920,209 | 4/1990 | Davis et al. .................. | 435/235 |
| 4,946,945 | 8/1990 | Wojdani . | |
| 4,981,693 | 1/1991 | Higashi et al. . | |
| 4,996,058 | 2/1991 | Sinnreich et al. .................. | 424/462 |
| 5,049,390 | 9/1991 | Wojdani . | |
| 5,202,159 | 4/1993 | Chen et al. .................. | 427/213.31 |
| 5,236,713 | 8/1993 | Wato et al. . | |

FOREIGN PATENT DOCUMENTS

| | | |
|---|---|---|
| 0277741 | 8/1988 | European Pat. Off. . |
| WO90/004963 | 5/1990 | WIPO . |
| 9004963 | 5/1990 | WIPO . |
| WO92/06708 | 2/1992 | WIPO . |

OTHER PUBLICATIONS

Sayegh, M.H. et al., Induction of Immunity and Oral Tolerance with Polymorphic Class II Major Histocompatibility Complex in the Rat, Proc. Natl. Acad. Sci. USA (1992) 89:7762–7766.

Ewguall, E., et al., Enzyme Linked Immunosorbant Assay ELISA III Quantitation of Specific Antibodies by Enzyme Labeled Anti–immunoglobulin in Antigen Coated Tubes, J. Immunol. (1972) 109:129.

Van Metre, T.E., Jr., et al., Immunotherapy for Aeroallergen Disease in Middleton, E. Jr., Reed, C.E., Ellis, F.F., Adkinson, N.R. Jr., (eds): Allergy Principles and Practice, Ed. 3, vol. II, St. Louis, CV Moshy, (1988) p. 1336.

Creticos, P.S., Immunologica Change Associated with Immunotherapy, Immunol. Aller. Clin. N. American, (1992) 12:13.

Hoffman, D., The Use and Interpretation of RAST to Stinging Insert Venom, Ann. Allergy, (1979) 43:224.

Eldridge, J.H. et al., Controlled Vaccine Release in the Gust-associated Lymphoid Tissues. I. Orally Administered Biodegradable Microcapsules Target to the Peyer's Patches, J. Controlled Release, (1990) 11:205–214.

O'Hagan, D.T., et al., Biodegradable Microparticle as Controlled Release Antigen Delivery System, Immunology (1991) 73:239–242.

Mowat, A.M., The Regulation of Immune Responses to Dietary Protein Antigens, Immunol. Today (1987) 8:93.

Adorini, L., et al., Approaches Toward Peptide Based Immunotherapy of Autoimmune Diseases, Springer Seminars Immunopathology (1992) 14:187–199.

Wong, George K., Development of Novel Oral Enteric–Coated Aquaculture Vigro Vaccines (1990) (unpublished Ph.D. thesis, Oregon State University, available from UMI Dissertation Services).

Moldoveanu et al., 1993. J. Infect. Disease 167:84–90.

Wheeler et al., 1987. Int. Arch. Allergy Appl. Immunol. 83(4):354–8.

Lai, 1985. Diss. Abs. Int. 49(10B):4254.

Waldman et al., 1986. Amer. J. Med. Sci. 292(6):367–71.

Fukumori, et al., 1988(a). Chem. Pharm. Bull. 36(12):4927–32.

Fukumori, et al., 1988. Chem. Pharm. Bull. 36(8):3070–78.

Langer, et al., 1990. Science 249:1527–1533.

Murray, et al., 1990. Aus. J. Hospital Pharm. 20(3):235–38.

Childers et al., Regional Immunology vol. 3(6), 289–296, 1990/1991).

Langer, 1990, New Methods of Drug delivery. Science 249: 1527–1533.

Murray et al. 1990. Gastric Residence times of Enteric Coated Dosage forms–A Review. Aus. J. Hosptial Pharm. 20(3):235–38.

(List continued on next page.)

*Primary Examiner*—James C. Housel
*Assistant Examiner*—N. M. Minnifield
*Attorney, Agent, or Firm*—Wood, Herron & Evans, P.L.L.

[57] ABSTRACT

An orally administrable therapeutic protein is provided by combining the therapeutic protein with a stabilizing agent in an aqueous solution. The solution is coated onto nonpareils and microencapsulated with a water emulsifiable enteric coating composition. The microcapsules are orally administered. The coating protects the protein as it passes through the stomach. Upon reaching the small intestines, the basic pH of the intestinal juices will dissolve the coating, allowing the protein to be released and induce antigen specific immune response which has the specificity of the native molecule. The stabilizing agent protects the therapeutic protein from denaturation during the encapsulation process.

20 Claims, 3 Drawing Sheets

OTHER PUBLICATIONS

Lai, 1985, Design and evaluation of waterbased pseudolatex enteric coating systems. Dissabs. vol. 49 No. 10B p. 4254.

Fukumori et al., 1988(A), Coating of pharmaceutical powders by fluidized bed process. IV. Softening . . . Chem. Pharm. Bull. 36(12):4927–32.

Fukumori et al 1988, Coating of pharmaceutical powders by fluidized bed process. III. Aqueous . . . Chem. Pharm. Bull. 36(8):3070–78.

Wong 1990 Development of novel oral enteric–coated aqua culture vibrio vaccines . . . Dissabs. Int. 52(5B):2519.

ORAL ADMINISTRATION OF THERAPEUTIC PROTEINS FOR TREATMENT OF INFECTIOUS DISEASE

This is a division of application Ser. No. 08/329,685, filed Oct. 26, 1994, which is a continuation of application Ser. No. 08/178,503, filed 7 Jan. 1994, abandoned, which is a continuation-in-part of application Ser. No. 07/994,932, filed Dec. 22, 1992 now abandoned, which is a continuation of application Ser. No. 07/719,160, filed Jun. 21, 1991, entitled "Orally Administrable Therapeutic Proteins and Method of Making," now abandoned.

BACKGROUND OF THE INVENTION

Immune response in mammals, including humans, is most predictably induced by parenteral (injectable) administration of a protein antigen. Oral administration of a protein antigen is usually an ineffective route of immunization. Indeed, oral administration of a protein may be immunosuppressive rather than immunogenic (Mowat, A. M. 1987, "The Regulation of Immune Responses to Dietary Protein Antigens," *Immunol. Today*, 8: 93). Thus, development of a method for efficient oral immunization would be extremely desirable. Immunization has beneficial therapeutic effects in many areas of clinical medicine. Specifically, antimicrobial vaccines consisting of bacteria, viruses and their products are beneficial in preventing and combating infections. Also, allergy immunotherapy, a treatment in which injections of small doses of allergens results in alleviation of allergy symptoms, is important in therapy of inhalant allergies, venom allergies and anaphylaxis. Finally, treatment of autoimmune diseases with autoantigens or their components can alleviate the autoimmune diseases, as discussed in PCT application W092/06708. Luciano Adorini, et al., *Approaches Toward Peptide Based Immunotherapy of Autoimmune Diseases Springer Seminar in Immunopathology Immunoprotein* (1992)14: 187–199. Further, rejection of transplanted organs can be reduced by injection of MHC Class I and Class II antigens. Mohamed H. Sayegh, et al., *Induction of Immunity and Oral Tolerance With Polymorphic Class II Major Histocompatibility Complex in the Rat*, Proc. Nat. Acad. Sc. USA (1992) 89 7762–7766.

Collectively, we refer to these proteins as therapeutic since they exert a therapeutic effect through activating the immune system of humans and mammals. These immunotherapeutic proteins are all susceptible to proteolytic enzymatic digestion and other denaturing and degrading processes such as acid pH digestion.

Immunization by oral administration of therapeutic proteins has been quite ineffective in the past. It is believed that these proteins are damaged or destroyed by gastric and intestinal juices, thus losing their immunogenicity by the time they reach the lymphoid (immune) tissue in the gastrointestinal tract.

SUMMARY OF THE INVENTION

The present invention is premised on the realization that an orally administrable therapeutic protein can be formed by microencapsulating a therapeutic protein with a coating which is insoluble under acid conditions and resistant to proteolytic digestion. Such conditions are encountered in the mammalian stomach and part of the small intestines. Preventing exposure to acid and proteolytic digestion preserves antigenic structure of the protein and its ability to immunize.

The present invention is further premised on the realization that by microencapsulating the protein under totally aqueous conditions without employing any nonequeous solvents, the structure and the immunogenicity of the protein remains intact.

More particularly, the present invention is premised on the realization that the therapeutic proteins should be coated with an acid stable coating under totally aqueous conditions so that they can pass through the stomach without being digested and then released intact into the small intestines where they can exert their therapeutic and/or immunological activity. In a preferred embodiment, the enteric coating is a water emulsion of erhylacrylate methylacrylic acid copolymer, or hydroxypropyl methyl cellulose acetate succinate (HPMAS).

The objects and advantages of the present invention will be further appreciated in light of the following detailed description and drawings.

DETAILED DESCRIPTION

Figure 1:
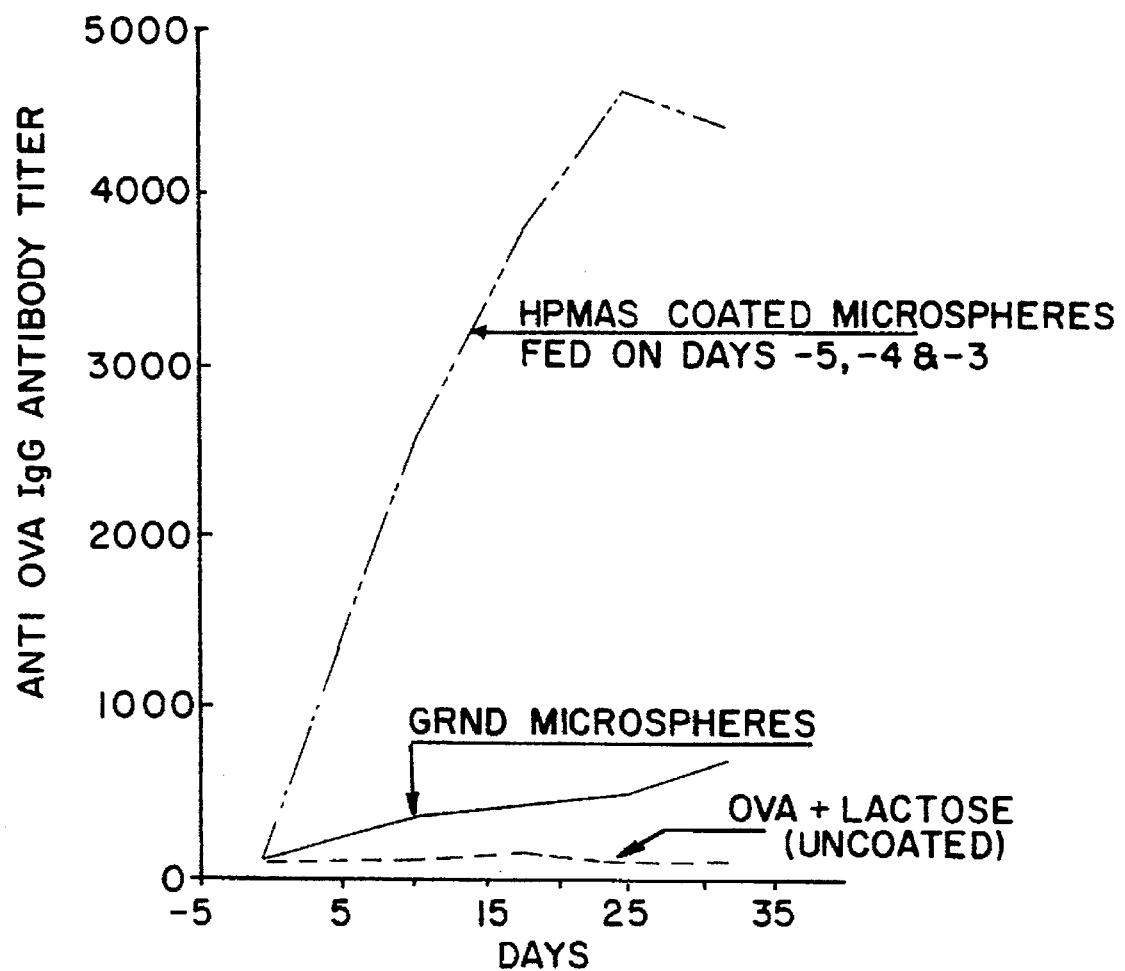
FIG. 1 is a graph depicting anti-OVA (hen egg albumin) IgG antibody titers of mice fed hydroxypropylmethyl cellulose acetate succinate (HPMAS) coated OVA containing microspheres or ground coated OVA microspheres or OVA in solution.

According to the present invention, an orally administrable therapeutic agent such as a protein or protein containing virus or bacteria is formed by microencapsulating the therapeutic protein with an enteric coating. This is generally referred to as the therapeutic protein.

The therapeutic agents are dispersed in an aqueous solution. The aqueous solution is then sprayed onto nonpareils. Subsequently the microspheres are coated with a water emulsion of a polymer which upon solidification is acid resistant. This protects the therapeutic protein as it passes through the stomach and releases it into the small intestines where it can act upon the lymphoid tissue.

Therapeutic proteins include microbial vaccines which include viral, bacterial and protozoal vaccines and their various components such as surface antigens. These include vaccines which contain glycoproteins, proteins or peptides derived from these proteins. Such vaccines are prepared from *Staphylococcus aureus*, *Streptococcus pyogenes*, *Streptococcus pneumoniae*, *Neisseria meningitidis*, *Neisseria gonorrhoeae*, Salmonellae species, Shigellae species, *Escherichia coli*, Klebsiellae species, Proteus species, *Vibrio cholerae*, *Helicobacter pylori*, *Pseudomonas aeruginosa*, *Haemophilus influenzae*, *Bordetella pertussis*, *Branhamella* catarrhalis, Mycobacterium tuberculosis, Legionella pneumophila, Pneumocystis carinii, Treponema pallidum and Chlamydiae species, tetanus toxoid, diphtheria toxoid, influenza viruses, adenoviruses, paramyxoviruses, rubella viruses, polioviruses, hepatitis viruses, herpesviruses, rabies viruses, HIV-1 viruses, HIV-2 viruses, and papilloma viruses. Other therapeutic proteins include those used for the treatment of autoimmune disease and to prevent transplant rejection.

In obtaining bacteria preparations, it is preferable to employ lyophilized bacteria which can be purchased or obtained by growing the bacteria, killing them with heat, washing them, followed by lyophilization.

Autoimmune disease is a disease in which the body produces an immunogenic response to some constituent of its own tissue. An autoimmune disease can be classified into those which predominantly affect one organ, such as hemolytic anemia and chronic thyroiditis, and those in which the autoimmune disease process is diffused through many tissues, such as multiple sclerosis, systemic lupus erythematosus, and arthritis. Exemplary autoimmune diseases and corresponding auto antigens include:

| Autoimmune disease | Therapeutic Protein |
|---|---|
| Multiple Sclerosis | Myelin basic protein |
| Myasthenia Gravis | Acetyl choline receptor |
| Rheumatoid Arthritis | Type II collagen |
| Diabetes Mellitus | Insulin |
| Juvenile Diabetes Mellitus | Insulin |
| Autoimmune Thyroiditis | Thyroid proteins |

One of the primary problems with transplanting organs is rejection of the organs. The immune system of the recipient can be treated to reduce rejection by use of a therapeutic protein. The therapeutic protein itself is the major histocompatibility complex (MHC) protein. MHC proteins are divided into two major groups: MHC I and MHC II. Either or both may serve as a therapeutic protein, as well as peptides derived therefrom, i.e., fragments or synthetic peptides derived from known amino acid sequences of the protein.

A second component which can be added to the therapeutic protein is a stabilizing agent. Stabilizing agents provide physical protection for the protein. Generally these stabilizing agents are therapeutically inactive water soluble sugars such as lactose, mannitol and trehalose. These act to protect the therapeutic antigen during the coating process and passage through the gastrointestinal tract.

To form orally administrable microcapsules for use in the present invention, an aqueous solution of the therapeutic protein and the optional stabilizing agent is formed. The aqueous solution will include generally from about 0.5 to about 10% by weight of the therapeutic protein with about 1% being preferred, and from about 1% to about 10% by weight of the stabilizing agent with about 5% being preferred. It is desirable to add 1–10% of polyvinylpyrrolidone to bind the therapeutic protein to the nonpareil and act as a bioadhesive agent for the protein during the passage through the gastrointestinal tract.

Nonpareils are small, round particles of pharmaceutically inert materials. Generally nonpareils formed from the combination of sucrose and starch are preferred. One such brand is Nupareils which is sold by Ingredient Technology Corporation. The preferred size is 30–35 mesh.

The nonpareils are coated with the aqueous solution of the therapeutic protein, the stabilizing agent, and bioadhesive agent to provide a coating of 1–30% by weight on a solids basis. Glatt brand powder coater granulators such as the GPCG-1, GPCG-5, or GPCG-60 fluid bed coaters are suitable for use in this application. Coating conditions and times will vary depending on the apparatus and coating viscosity. But, generally all coating steps must be conducted at less than 50° C., preferably less than 35° C. to avoid denaturing the protein.

The protein coated microspheres are dried and subsequently coated with an acid stable polymer (enteric coating). Generally, the coating will be applied in the same manner as the protein with the same equipment.

The coating composition used in the present invention is preferably a water based emulsion polymer. The preferred coating is an ethylacrylate methacrylic acid copolymer sold under the trademark Eudragit L 30D manufactured by Rhom Pharma. This has a molecular weight of about 250,000 and is generally applied as a 30% aqueous solution. An alternate coating is hydroxypropylmethyl cellulose acetate succinate.

The coating composition can be combined with a plasticizer to improve the continuity of the coating. There are several well known plasticizers typically used. Triethyl citrate (TEC) sold by Morfley Inc. is preferred. This can form about 1–30% of coating composition. Although plasticizers can be liquid, they are not considered to be solvents since they lodge within the coating altering its physical characteristics. They do not act to dissolve the protein. Any plasticizer which dissolves or denatures the protein would be unacceptable.

Talc (3.0% of coating composition) can also be added to prevent sticking between the particles if desired. Also, an antifoaming agent (0.0025% of coating composition) such as sorbitan sesquioleate (Nikko Chemicals Company Limited) or silicone can be added. Both the talc and antifoaming agent are added only if needed.

The microspheres coated with the therapeutic protein and optional stabilizing and bioadhesive agents, are dried and are then coated with the enteric coating as previously described. The coating solution is about 30% polymer, 0–30% plasticizer, 0 to 3% talc and 0 to 0.0025% antifoaming agent and water. It is important that there be no organic solvents including alcohols and even glycols present in the coating composition. The presence of these solvents during coating application can denature the therapeutic protein. The coating is conducted in the same equipment used to coat the nonpareils with therapeutic protein. The temperature for this coating should be about 30° C. but less than 50° C.

In an alternate embodiment of the present invention, a therapeutically acceptable water dispersible aluminum compound such as aluminum sulfate or aluminum hydroxide are added to the aqueous dispersion or solution of protein prior to coating onto the nonpareil. This acts to increase immunogenicity of the proteins. Generally 1% to 10% of aluminum compound is added.

The enteric coated microspheres then can be placed in gel capsules for oral administration to humans. Dosage will depend on the individual and the course of the therapy. Generally, the dosages will be the same as dosages used for treatment when administered by injection. With transplant rejection, the dosage may vary greatly, depending on the patient's immune system. Generally, the dosage will be 0.1 to 100 mg administered daily starting about two weeks prior to transplant in order to induce a state of tolerance to a foreign graft (organ tissue or cell) and may continue post-transplant in order so maintain the tolerant state. Thereafter a lower maintenance dose can be administered daily.

For autoimmune treatment, the autoantigen, fragment, or analog is introduced orally in an amount of from 0.1 to 1000 mg per day, and may be administered in single dose form or multiple dose form. Preferably, the autoantigen, fragment or analog is administered in an amount of from 0.1 mg to 500 mg per day. As is understood by one skilled in the art, the exact dosage is a function of the autoantigen, the age, sex and physical condition of the patient, as well as other concurrent treatments being administered. Such preparations may be administered to an animal in need of treatment for such autoimmune disease so as to ameliorate, relieve, alleviate, reverse, or lessen the severity of the disease. Such preparations may also be administered to an animal who is predisposed to developing such autoimmune disease so as to prevent the onset of such disease or to lessen the severity of such disease when it does emerge.

The bacteria and viral dosage, again, is the same as the injected dosage—generally 10 µg to 10 mg. A single dosage should be effective, however repeated lower dosages may be preferred to slowly build up the immunity.

The invention will be further appreciated in light of these following examples. In many of these examples OVA is tested in mice as a model. Human study with allergens has shown this to be quite indicative of human response. The mouse model is, of course, generally accepted in the study of infectious disease.

EXAMPLE 1

Immunogenicity of Encapsulated OVA

Immunological properties of OVA released from microspheres were tested following oral administration to 6–8 weeks old BDF mice. Control groups of mice were fed with unencapsulated OVA (OVA and lactose) or ground enteric coated microspheres. The enteric coating was hydroxy propyl methyl cellulose acetate succinate sold by Shin Etsu Chemical Company which was applied in an aqueous suspension. (10% HPMCAS, 2.8% TEC, 3.0% talc, 0.0025% Sorbitan Sesquioleate.)

The OVA preparations were fed to BDF mice as described in FIG. 1. Subsequently the mice were bled and their serum anti OVA IgG antibody levels determined by ELISA (Emguall, E., Perlman, P., 1972, "Enzyme Linked Immunosorbant Assay ELISA III Quantitation of Specific Antibodies by Enzyme Labeled Anti-immunoglobulin in Antigen Coated Tubes," *J. Immunol.*, 109: 129). As shown in FIG. 1, oral administration of encapsulated OVA resulted in significant immune response to the specific antigen. Unencapsulated OVA preparations were poorly immunogenic.

EXAMPLE 2

Properties of Encapsulated OVA

Figure 2:
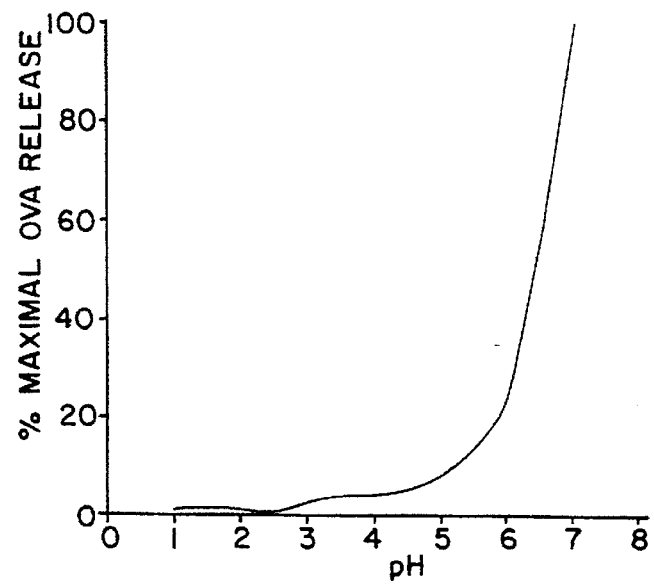
FIG. 2 is a graph depicting the release of hen egg albumin (OVA) from enteric coated microspheres after two hours in solutions at various pH.
Figure 3:
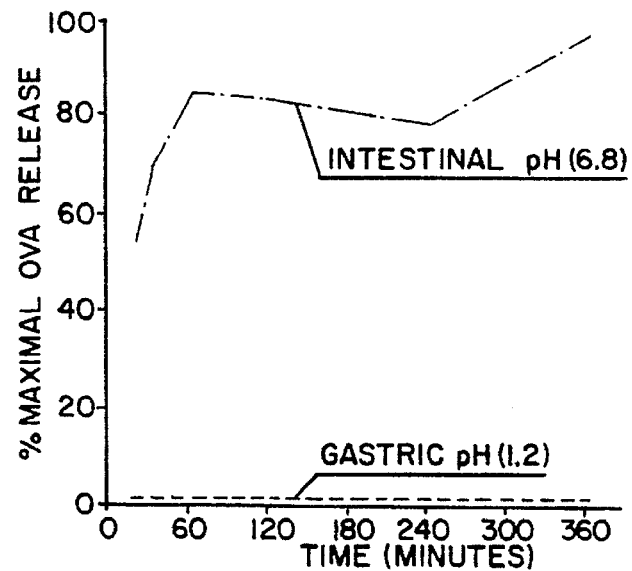
FIG. 3 is a graph depicting OVA released over time from enteric coated microspheres in solutions at gastric (1.2), or intestinal pH (6.8)

OVA coated nonpareils were prepared from 20 grams of nonpareils, 1 gram of OVA, 1 gram PVP, and 1 gram of lactose. These were then coated with Eudragit L30D in a total aqueous system (7 grams Eudragit L30D and 23 grams coated nonpareils). These were initially tested to determine resistance to acid pH typically encountered in the gastric juices. As shown in FIG. 2, the OVA was not released until the pH approached 6. At pH 6 to 7, substantially all of the OVA was released. To determine the release of OVA over time, these microspheres were exposed to either intestinal pH of 6.8 or gastric pH of 1.2 (FIG. 3). At the gastric pH of 1.2, virtually none of the OVA was released for 6 hours. However, at pH 6.8, substantially all of the OVA was released in a short time. OVA released from the microspheres was tested for antigenicity and immunogenicity. It was demonstrated that the released antigen retained its native structure (ELISA inhibition assay), and was as immunogenic as the untreated OVA (data not shown). Immune responses to all therapeutic antigens described below were always measured against native antigens by ELISA assay, thus proving that the encapsulated antigens retained their native structure.

EXAMPLE 3

Immunogenicity of Encapsulated OVA

Figure 4:
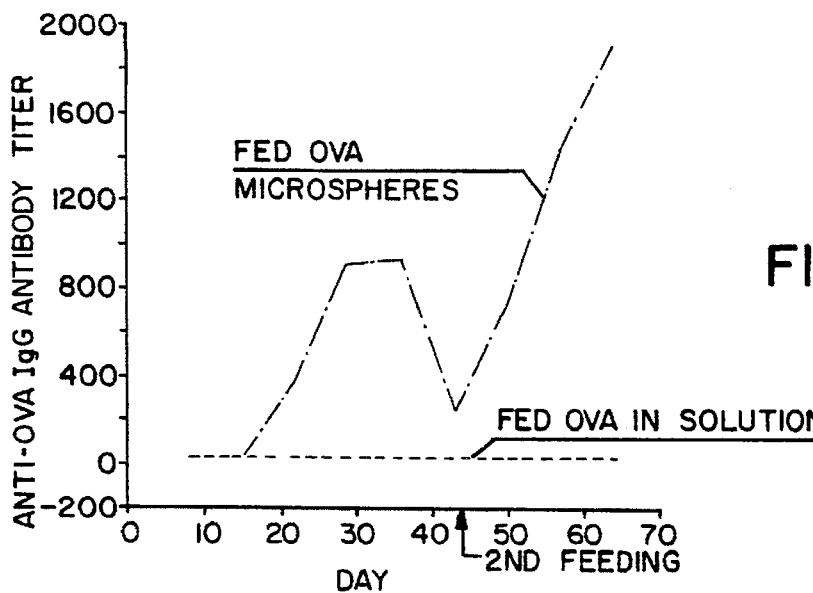
FIG. 4 is a graph showing IgG antibody response to OVA in naive mice following the feeding with OVA (1 milligram per day for 3 days) as enteric coated microspheres or OVA in solution.

The enterocoated microspheres containing OVA as described above were fed to 6–8 weeks old female BDF mice, (1 mg OVA per day for 3 days in microspheres or alternately in solution). Anti-OVA antibody titer (IgG) of the mice fed OVA microspheres coated with Eudragit L30D rose significantly after the 3 days feeding and continued to rise after a second feeding at day 42. Mice fed OVA in solution did not develop antiOVA antibodies. The results are shown in FIG. 4.

EXAMPLE 4

Immunogenicity of Microspheres Containing Diphtheria Toxoid in Mice

Figure 5:
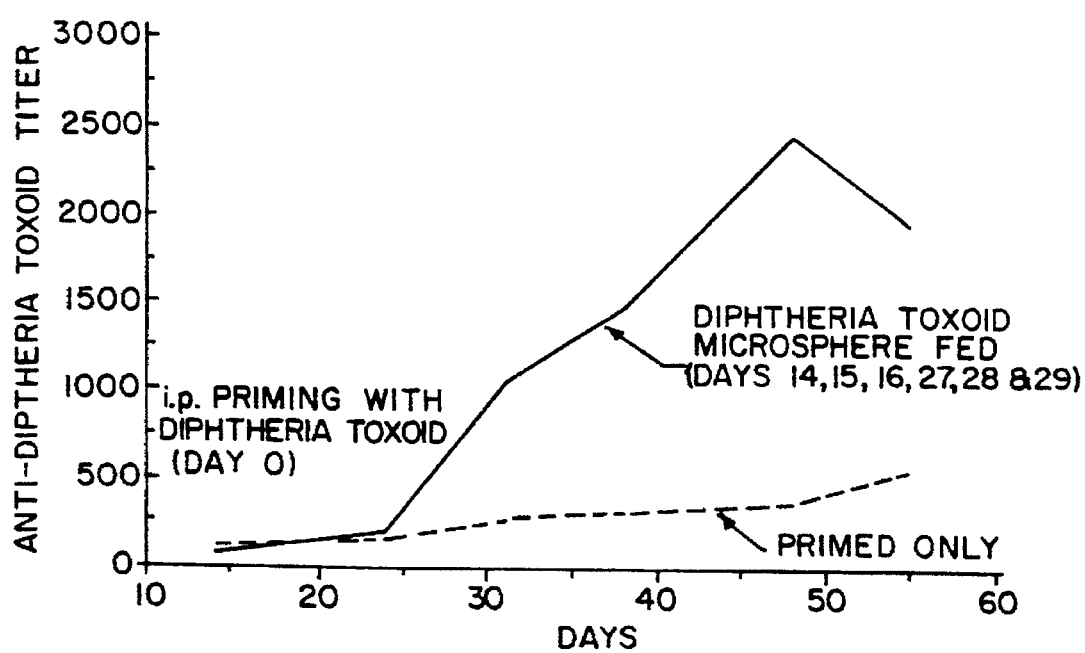
FIG. 5 is a graph showing the anti-diphtheria toxoid titer in mice primed with diphtheria toxoid and fed enteric coated diphtheria toxoid microspheres primed with diphtheria toxoid without subsequent immunization.

Diphtheria toxoid was obtained from Lederle Laboratories, Pearl River. Six ml of the toxoid concentrate and 3 gm PVP suspended in 200 ml water were coated onto nonpareils and subsequently coated with a solution of 33.3 gm Eudragit L30D (30% solids) and 1.1 gm triethyl citrate. Microspheres were orally administered to mice. Microspheres containing 1 Lf diphtheria toxoid were fed on days 14, 15, 16, and 27, 28, and 29.) All mice (DF females 6–8 weeks old) were immunized i.p. with 1 Lf units of diphtheria toxoid in alum on day 0. Mice fed diphtheria toxoid microspheres produced significantly increased levels of specific antibodies compared to mice that were just primed (FIG. 5).

EXAMPLE 5

Adjuvant Effect of Alum in Microspheres

Figure 6:
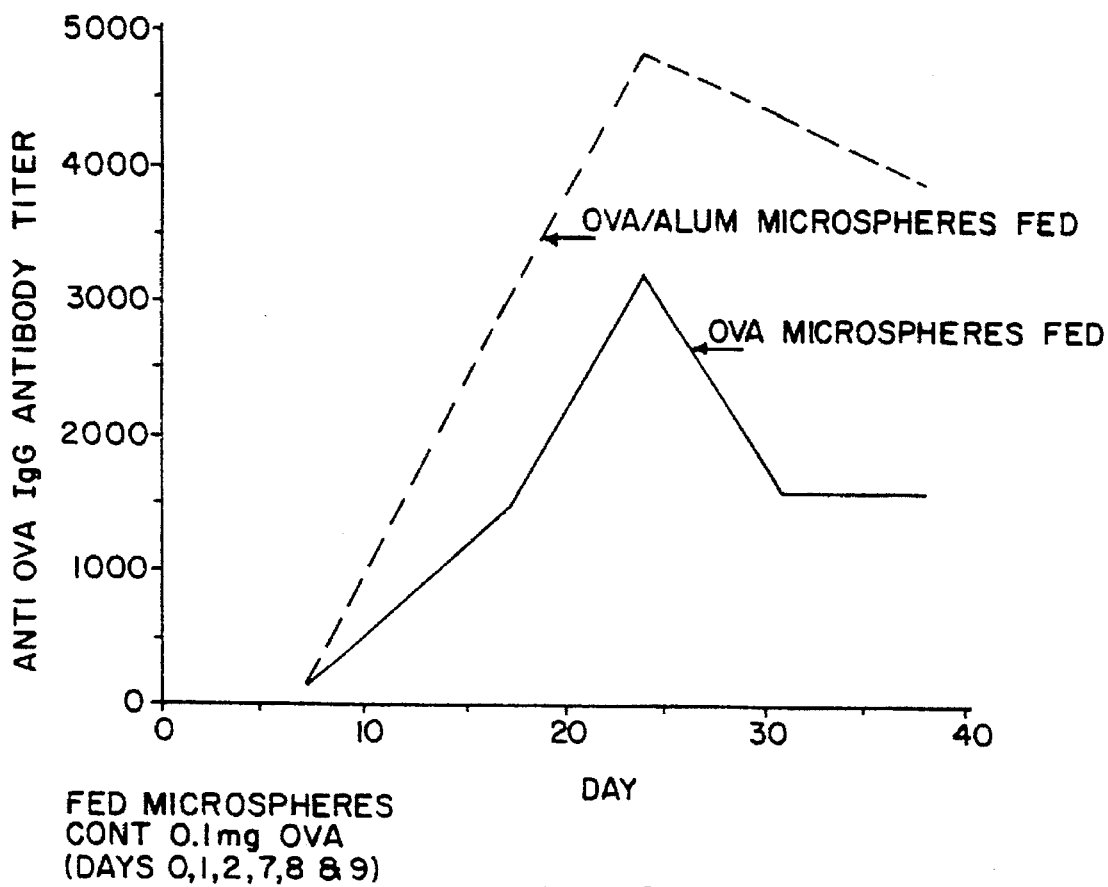
FIG. 6 is a graph showing IgG antibody titers of mice fed enteric coated microspheres containing OVA or OVA and aluminum hydroxide.

The addition of aluminum hydroxide to a therapeutic protein (OVA) was tested. OVA was adsorbed on aluminum hydroxide by mixing the protein with the aluminum hydroxide in a ratio 1:2 by weight. The mixture was suspended in water and sprayed on non-pareils which were then enteric coated with Eudragit L30D. The conditions of encapsulation were the same as described earlier for OVA encapsulation. The immune response in 6 week old BDF mice to encapsulated OVA-aluminum hydroxide mixture was significantly greater than observed for encapsulated OVA prepared without aluminum hydroxide as determined by measurement of antiOVA IgG antibody titers (FIG. 6).

EXAMPLE 6

Encapsulated Bacterial Vaccine

*E. coli* bacteria, strain 0120:B8, an enteropathogen, was purchased from ATCC. The bacteria were grown overnight in Difco nutrient broth at 37° C. and subsequently washed three times in sterile saline. The bacteria were killed by heating at 100° C. (boiling water bath) for five minutes. The bacterial killing was verified by lack of growth in nutrient broth. The killed bacteria were washed three times in sterile, distilled water, lyophilized and encapsulated by the technology as described earlier. BDF mice were immunized by oral administration of the encapsulated bacteria and the immune response measured by ELISA.

EXAMPLE 7

Treatment of Multiple Sclerosis Patients

An aqueous solution of bovine myelin basic protein is coated onto nonpareils with the addition of lactose and PVP and dried as previously described. The coated nonpareils are coated with Eudragit L30D as previously described.

The myelin is administered to patients with multiple sclerosis in capsules containing 1 mg of the myelin basic protein daily. This is continued until the patient's disease is in remission.

EXAMPLE 8

Treatment of Patients with Rheumatoid Arthritis

An aqueous solution of chicken Collagen II antigen is coated onto nonpareils with the addition of lactose and PVP, which are in turn coated with Eudragit L30D.

Capsules containing the Collagen II are fed to patients diagnosed with rheumatoid arthritis. The dosage is 0.1 mg per day. Once symptoms are relieved, a lower maintenance dosage can be used.

EXAMPLE 9

Transplant Rejection

An aqueous solution of major histocompatibility complex (MHC) proteins (MHC 1 and MHC II) are coated onto nonpareils along with lactose and PVP and coated with Eudragit L30D. Capsules containing the coated nonpareils are fed to patients two weeks prior to receiving a transplant. The dosage is 0.1 to 1 mg per day. The dosage requirement is continued indefinitely following transplant.

The present invention provides an oral treatment modality for a wide variety of conditions such as bacterial and viral infections, as well as treatment of autoimmune disease and prevention of transplant rejection. Denaturation of the therapeutic protein is avoided when coating the protein with an enteric coat. The prevention of denaturation was demonstrated by measuring immune responses to these proteins against native, unmodified antigens. If the antigens were denatured during encapsulation, antibody produced against this molecule would not react with the native antigen. Furthermore, the coating provides protection against low pH and enzymatic degradation enabling delivery of the intact molecule into small intestine. These beneficial effects of orally administered antigens are evidenced by induction of IgG immune response in animals. The efficacy of the immune response can be further enhanced by the addition of an aluminum compound.

The preceding has been a description of the present invention along with the preferred method currently known of practicing the invention. While there are many minor modifications that can be made without departing from the scope of the present invention, the scope of the present invention should be defined by the appended claims wherein we claim:

What is claimed is:

1. An orally administrable immunogenic composition for activating the immune system of a warm-blooded animal comprising:
   at least one immunogen of a microbial organism infectious for said warm-blooded animal microencapsulated in the complete absence of organic solvents with a water based enteric coating.

2. The composition claimed in claim 1 wherein said enteric coating is a water based emulsion of an ethylacrylate methacrylic acid copolymer.

3. The composition claimed in claim 1 wherein said microbial organism is a bacterium selected from the group consisting of *Staphylococcus aureus*, *Streptococcus pyogenes*, *Streptococcus pneumoniae*, *Neisseria meningitidis*, *Neisseria gonorrhoeae*, Salmonellae species, Shigellae species, *Escherichia coli*, Klebsiellae species, Proteus species, *Vibrio cholerae*, *Helicobacter pylon*, *Pseudomonas aerugtnosa*, *Haemophilus influenzae*, *Bordetella pertussis*, *Branhamella catarrhalis*, *Mycobacterium tuberculosis*, *Legionella pneumophila*, *Pneumocystis carinii*, *Treponema pallidum* and Chlamydiae species.

4. A method of administering an immunogen for activating the immune system of a warm-blooded animal comprising orally administering to said animal an amount of the composition claimed in claim 1 effective for activating the immune system of said animal.

5. The composition of claim 1 wherein said immunogen comprises a bacterial toxoid selected from the group consisting of diphtheria toxoids and tetanus toxoids.

6. The composition of claim 1 wherein said immunogen comprises killed bacteria.

7. The composition of claim 1 wherein said immunogen is selected from the group consisting of proteins, peptides, glycoproteins and whole microbial organisms.

8. The composition of claim 1 wherein said microbial organism is a protozoan microorganism.

9. An orally administrable immunogenic composition for activating the immune system of a warm-blooded animal comprising:
   at least one immunogen therapeutic for said warm-blooded animal microencapsulated in the complete absence of organic solvents with a water based enteric coating.

10. A method of administering an immunogen for activating the immune system of a warm-blooded animal comprising orally administering to said animal an amount of the composition claimed in claim 9 effective for activating the immune system of said animal.

11. The composition of claim 9 wherein said composition further comprises an adjuvant which increases immunogenicity of said immunogen.

12. The composition of claim 9 wherein said immunogen is microencapsulated on particles of a pharmaceutically inert material having a first coating comprising said immunogen and a second coating comprising said enteric coating.

13. The composition of claim 12 wherein said first coating further comprises at least one of a stabilizing sugar, a binding agent to bind the immunogen to said particles, and a bioadhesive agent for adhering the immunogen in the gastrointestinal tract.

14. The composition of claim 13 wherein said stabilizing sugar comprises lactose.

15. The composition of claim 13 wherein said stabilizing sugar comprises trehalose.

16. The composition of claim 13 wherein said binding agent comprises polyvinylpyrrolidone.

17. The composition of claim 13 wherein said bioadhesive agent comprises polyvinylpyrrolidone.

18. The composition of claim 12 wherein said second coating further comprises a plasticizer.

19. The composition of claim 18 wherein said plasticizer comprises triethyl citrate.

20. An orally administrable immunogenic composition for activating the immune system of a warm-blooded animal comprising:

at least one immunogen therpeutic for said warm-blooded animal microencapsulated in the complete absence of organic solvents with a water based enteric coating, wherein said immunogen is microencapsulated on particles of a pharmaceutically inert material with a first coating comprising said immunogen, lactose or trehalose, and polyvinylpyrrolidone, and a second coating comprising said enteric coating and triethyl citrate.

\* \* \* \* \*